United States Patent [19]

Kimbell

[11] 4,114,419
[45] Sep. 19, 1978

[54] METHOD OF TESTING AN ANALYZER TO DETERMINE THE ACCURACY THEREOF AND A VOLUMETRIC PRIMARY STANDARD APPARATUS FOR DOING SAME

[76] Inventor: Charles L. Kimbell, P.O. Box 40052, Houston, Tex. 77041

[21] Appl. No.: 803,675

[22] Filed: Jun. 6, 1977

[51] Int. Cl.² .......................................... G01N 31/00
[52] U.S. Cl. ........................................................ 73/1 G
[58] Field of Search ........................... 73/1 G, 422 GC

[56] References Cited

U.S. PATENT DOCUMENTS 3,521,674  7/1970  Dodson ........................... 73/422 GC
3,911,723  10/1975  Ritter .................................... 73/1 G

FOREIGN PATENT DOCUMENTS 811,973  5/1969  Canada ...................................... 73/1 G

OTHER PUBLICATIONS

Ritter et al., Analytical Chemistry, vol. 48, No. 3, Mar. 1976, pp. 612–619.

*Primary Examiner*—S. Clement Swisher
*Attorney, Agent, or Firm*—Pravel, Wilson & Gambrell

[57] ABSTRACT

A method of testing an analyzer to determine the accuracy thereof and a volumetric primary standard apparatus for doing same, the method of which includes flowing a carrier gas stream at a known flow rate, periodically injecting a measured quantity of sample gas at a selected interval into the carrier gas stream, homogeneously mixing the carrier gas and the sample gas therewith in a mixing chamber for providing a homogeneous mixture of sample gas and carrier gas and thereafter flowing the homogeneous mixture into an analyzer whose accuracy is to be tested.

14 Claims, 4 Drawing Figures

METHOD OF TESTING AN ANALYZER TO DETERMINE THE ACCURACY THEREOF AND A VOLUMETRIC PRIMARY STANDARD APPARATUS FOR DOING SAME

BACKGROUND OF THE INVENTION

The field of this invention is testing devices, particularly of the type used for testing the accuracy of an analyzer.

Prior art methods and apparatus for analyzer calibration and testing utilizing trace gases have taken the form of numerous, various types of systems. In one system, permeation tubes are used in such a fashion that permeation tube diffusion into a metered carrier gas flow is utilized for providing trace gases to an analyzer, such as that detailed in the article by Larry DeMaio of Mine Safety Appliances, Pittsburgh, Pa., entitled "Calibrating Trace Gas Analyzers Using Permeation Tubes", presented at the Eighteenth Annual Symposium of the Analysis Instrumentation Division of the Instrument Society of America, May 3–5, 1972 and published in Air Quality Instrumentation, Vol. 2, edited by J. W. Scales, Instrument Society of America, 1974, pages 229–241. Also, the article referenced Debbrecht, F. Jay and Neel, E. M, "Application and Description of a Portable Calibration System," *Calibration in Air Monitoring, ASTM STP* 598, American Society for Testing and Materials, 1976, pages 55–65, relates to systems based upon permeation tube techniques.

Other analyzer calibration techniques include dynamic dilution by means of a multi-stage process wherein the carrier gas and trace gas are measured by flow rate devices and mixed, with such techniques being detailed in the article Lucero, D. P., "Ultra Low-Level Calibration Gas Generation by Multi-Stage Dilution Techniques," *Calibration in Air Monitoring,* ASTM STP 598, American Society of Testing and Materials, 1976, pages 301–319. Still further, other systems utilize exponential dilution by diluting a gas in a fixed volume with a continous flowing carrier wherein the output concentration may be computed by formula.

Other techniques include passing a carrier gas over a liquid surface, with the carrier gas mixing with a pollutant gas in the liquid according to the partial pressure that the pollutant gas exerts over the liquid. Lastly, trace gases for analyzer calibration may be prepared by introducing a fixed volume of sample gas into a container of fixed volume of carrier gas to provide a given concentration of sample gas in the carrier gas.

However, with all prior art methods, typically low flow rates are difficult to accurately measure; or in the alternative, the sample gas-carrier gas mixtures, after preparation, tend to deteriorate with time due to absorption reactions, adsorption reactions, and permeatation, which tend to provide results which are unreliable for accurately calibrating an analyzer. Some prior art systems are dependent on flowing very small quantities of a sample gas in a carrier gas stream where measurements are not easily monitored, particularly in current, state of the art flow meters. Further, many of the permeation devices are subject to deviation if the temperature and barometric pressure are not held within a critical range. Fluctuations in temperature and the barometric pressure affect permeation rates which can and do affect the reliability of permeation tube devices.

Prior art devices include those such as disclosed in U.S. Pat. Nos. 2,927,465; 3,253,469; 3,362,228; 3,412,935; 3,479,880; 3,533,295; 3,535,939; 3,654,959; 3,681,996; 3,746,217; 3,751,992; 3,908,463; 3,915,013; and, 3,975,946. Of these references, it is useful to note that microliter valves in the past have been disclosed and used in the use of a chromatograph apparatus, which is well known in the art. However, the use of a microliter valve in a device for testing and calibrating the accuracy of an analyzer is believed to be heretofore unknown.

SUMMARY OF THE INVENTION

The present invention provides a new and improved method of testing an analyzer to determine the accuracy thereof and a volumetric primary standard apparatus for doing same wherein the method includes the steps of flowing a carrier gas stream at a known flow rate, periodically injecting a measured quantity of sample gas at a selected interval into the carrier gas stream, homogeneously mixing the carrier gas and sample gas therewith in a mixing chamber for providing a homogeneous mixture of sample gas and carrier gas and thereafter flowing the homogeneous mixture into an analyzer whose accuracy is to be tested.

The volumetric primary standard apparatus of the present invention provides a new and improved apparatus for rapidly and frequently determining whether the readings of an analyzer are accurate and includes mechanisms for flowing the carrier gas at a known rate and injecting periodic amounts of sample gas at selected intervals into such carrier gas as it is flowing, with transfer provisions for transferring the carrier gas and sample gas therewith to the mixing chamber wherein thorough mixing of the carrier gas and sample gas occurs to form a homogeneous flowing mixture for continuous flow therethrough for flow to an analyzer.

DESCRIPTION OF THE PREFERRED EMBODIMENT

Figure 1:
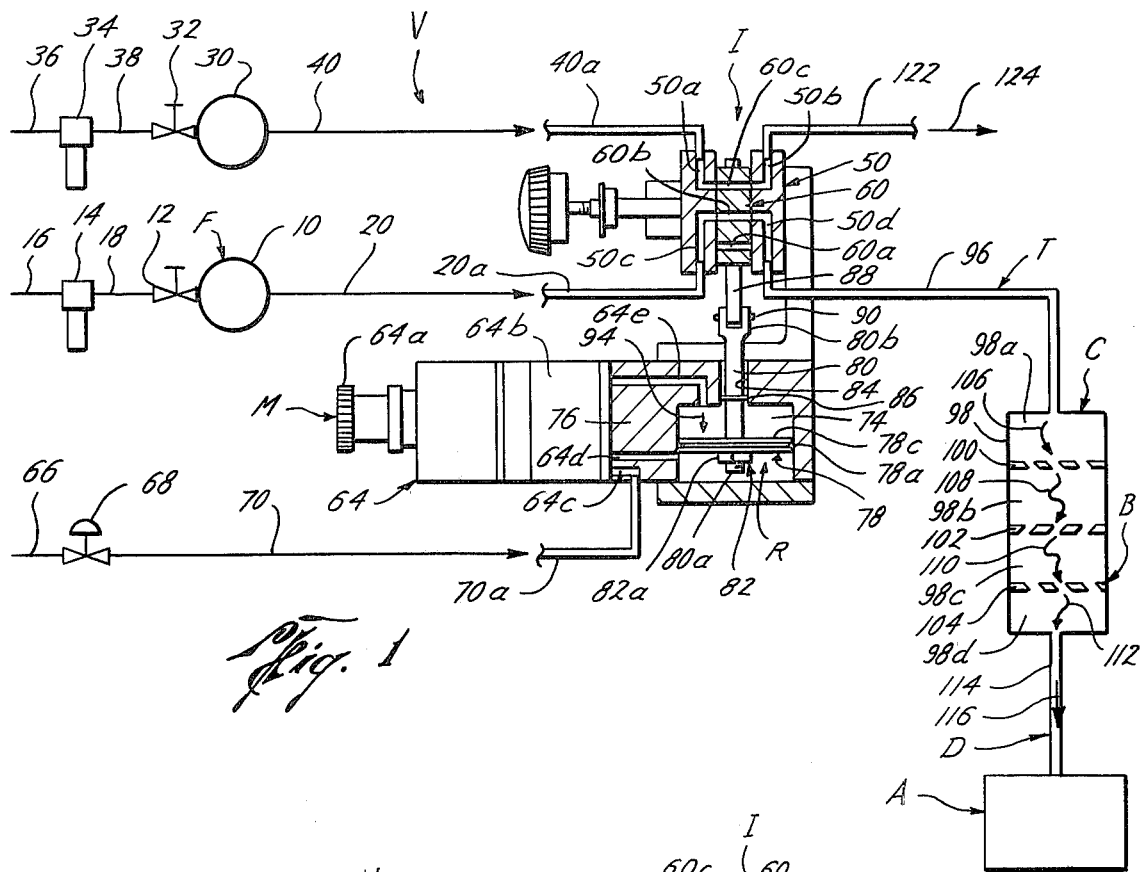
FIG. 1 is a partly schematic view of the volumetric primary standard apparatus of the present invention showing the injection means of the present invention partly in section and in the inject position.

In the drawings, the letter V designates the volumetric primary standard apparatus of the present invention. The volumetric primary standard apparatus V of the present invention includes flow means F for flowing a carrier gas at a known rate, injection means I connected with the flow means F for injecting periodic measured amounts of sample gas at selected intervals into the carrier gas as it is flowing through the injection means I, transfer means T for transferring the carrier gas and sample gas therewith from the injection means I to a mixing chamber C wherein thorough mixing of the sample gas and carrier gas results in a homogeneous flowing mixture for continuous flow through such chamber C for flow to an analyzer A.

Considering the invention in more detail, the volumetric primary standard apparatus V includes flow means F for flowing a carrier gas at a known rate. The flow means F includes any flow measuring device 10 such as a rotometer, wet-test meter, critical orifice, or a positive displacement pump and/or any other type of flow measuring device capable of accurately measuring and monitoring fluid flow. An appropriate valve 12 is mounted upstream of the flow measuring device for accurately regulating the fluid flow through the flow measuring device 10. A suitable filter 14 may be mounted upstream of the valve 12 for removing any unwanted impurities in the fluid flow. Preferably, conduit 16 connects the filter 14 with a source (not shown) of carrier gas. The carrier gas may include, by way of example but not limitation, such gases as hydrogen, nitrogen, air, or any other suitable carrier gas. Conduit 18 connects the filter 14 with valve 12 and flow measuring device 10, with conduit 20 connecting and permitting flow communication between the flow measuring device 10 and the injection means I by means of conduit 20a.

The volumetric primary standard apparatus V further includes a flow measuring device 30, valve 32 mounted adjacent the flow measuring device 30 and upstream thereof, and filter 34 upstream of valve 32. The flow measuring device 30, as flow measuring device 10, may be any device suitable for measuring flow such as a rotometer, wet-test meter, critical orifice, or positive displacement pump or any other suitable device. The valve 32, mounted upstream of flow measuring device 30, is used to regulate flow entering into the flow measuring device 30. Flow regulation through flow measuring device 30 need not be as critical as it is through flow measuring device 10, as detailed more fully hereinbelow. Conduit 36 is adapted to receive a sample gas, such as a 100% concentration of hydrogen sulfide by way of example, from a suitable source (not shown), being directed through conduit 36 into filter 34 for removing any undesired impurities therein. The sample gas flows through conduit 38 from filter 34 into valve 32, wherein valve 32 regulates the rate of flow of such sample gas entering into the flow measuring device 30 wherein such flow of sample gas is capable of being measured in the flow measuring device 30. The flow of sample gas is then directed through conduit 40 from the flow measuring device 30 into conduit 40a which is connected and in flow communication with the injection means I.

The volumetric primary standard apparatus V of the present invention includes injection means I connected to the flow means F for injecting periodic measured amounts of sample gas at selected intervals into the carrier gas as it is flowing through the injection means I. The injection means I includes a valve body 50 having a sample gas inlet port 50a mounted in flow communication with conduit 40a, a sample gas exit port 50b, a carrier gas inlet port 50c mounted in flow communication with conduit 20a, and mixture exit port 50d.

The injection means I of the volumetric primary standard apparatus V of the present invention further includes regulating means R for regulating the communication of the sample gas within the sample gas inlet port 50a with the carrier gas in the carrier gas inlet port 50c to be discharged from the valve body 50 through the mixture exit port 50d into the transfer means T and mixing chamber C. The regulating means R includes a slider block 60 that is movable with respect to the valve body 50 and is movable between a purge position (FIG. 2) and an inject position (FIG. 1), as described more fully hereinbelow.

Figure 2:
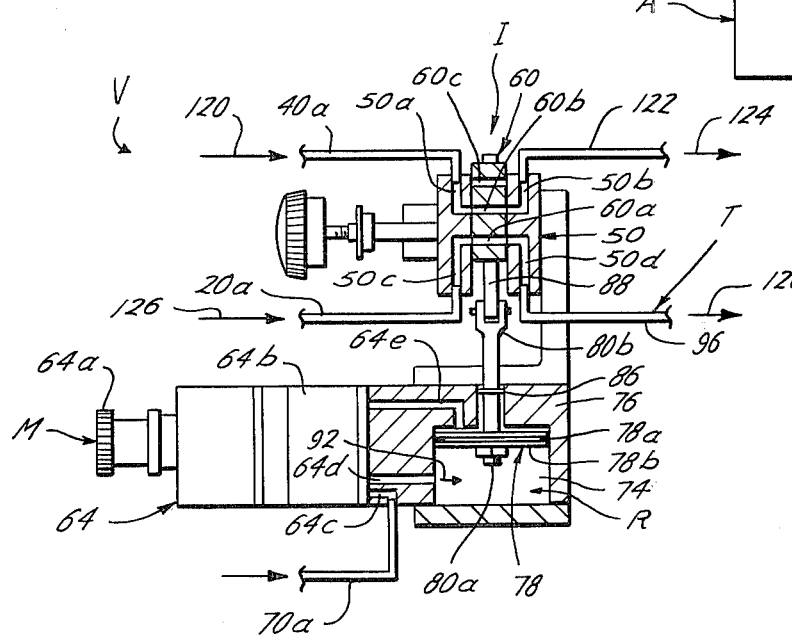
FIG. 2 is a sectional view of the injection means of the volumetric primary standard apparatus of the present invention in a purge position.

The slider block 60 includes a first chamber 60a, a second chamber 60b, and a third chamber 60c. In the purge position as shown in FIG. 2, the first chamber 60a communicates with the carrier gas inlet port 50c and mixture exit port 50d and second chamber 60b communicates with the sample gas inlet port 50a and the sample gas exit port 50b. As shown in FIG. 1, when the slider block 60 is in the inject position, the second chamber 60b communicates with the carrier gas inlet port 50c and mixture exit port 50d and the third chamber communicates with the sample gas inlet port 50a and the sample gas exit port 50b. The slider block 60 is movable between the purge position (FIG. 2) and the inject position (FIG. 1) within the valve body 50 having appropriate seal means (not shown) to prevent any fluid leakage between the slider block 60 and valve body 50 or between any non-adjacent chambers 60a, 60b, 60c and ports 50a, 50b, 50c, 50d.

The volumetric primary standard apparatus V of the present invention further includes timing means M mounted with the injection means I for regulating the rate of injection of the sample gas into the carrier gas at selected intervals. The timing means M includes timer 64 which may be an adjustable timer such as that manufactured by and identified as Miller Fluid Power No. 506620. Such a timer 64 typically includes an adjustable timing knob 64a. Such a timer may be electronic, having solenoid actuation or alternatively, as shown in FIGS. 1 and 2, the timing means M may be powered by a pneumatic source (not shown) affixed to and in flow communication with conduit 66 (FIG. 1), with valve 68 regulating and controlling the pneumatic flow through conduit 70, with conduit 70a being affixed to and in flow communication with timer body 64b at intake chamber 64c. The timer 64 directs the pneumatic flow in conduit 70a and intake chamber 64d at selected intervals alternately into passageways 64d, 64e, with each passageway 64d, 64e communicating with actuator chamber 74 formed in housing 76 with the timing means M.

The actuator chamber 74 is adapted to receive an actuator piston 78 having a suitable sealing means 78a mounted therewith for appropriately sealing the actuator piston 78a adjacent the walls of the actuator housing 74. The actuator piston 78 is mounted for reciprocal, vertical movement within the actuator chamber 74 in response to pneumatic impulses directed from the timing means M at selected intervals through either of the passageways 64d, 64e, respectively. An actuator shaft 80 is appropriately secured to the actuator piston 78 by suitable fastener 82, such as bolt 82a threadedly affixed to actuator shaft threaded end 80a, or by any other suitable fastener, for securing the actuator shaft 80 with the actuator piston 78. The actuator shaft 80 is adapted to be mounted in part within the actuator chamber 74 and extend vertically therefrom through opening 84 formed in the housing 76 with a suitable sealing means 86 provided between the actuator shaft 80 and opening 84 for preventing fluid migration therebetween.

Preferably, a yoke 80b is formed with the upper end of the actuator shaft 80 and adapted to receive therein arm 88 affixed to slider block 60, with arm 88 being pivotally affixed to the yoke 80b of actuator shaft 80 by pin 90. Reciprocal movement of the actuator piston 78 within actuator chamber 74 results in corresponding reciprocal movement of actuator shaft 80, arm 88 and slider block 60.

Upward vertical movement of the actuator piston 78 is effectuated by the timing means M directing pneumatic pressure through passageway 64d at a selected interval in the direction of arrow 92 (FIG. 2) acting on the bottom surface 78b of the actuator piston 78, forcing the actuator piston 78 upwardly within the actuator chamber 74. Alternatively, as shown in FIG. 1, pneumatic pressure is directed and regulated by the timing means M at a selected interval through passageway 64e in the direction of arrow 94 resulting pneumatic pressure acting on upper surface 78c of actuator piston 78 causing downward vertical movement of the actuator piston 78, actuator shaft 80, arm 88 and slider block 60. Rotation of the adjustable timing knob 64a of the timer 64 of the timing means M regulates the rate of switching or oscillation between passageways 64d, 64e for regulating the rate of vertical, reciprocal movement of the actuator piston 78, actuator shaft 80, arm 88 and slider block 60.

The injection means I and timing means M is available as a commercial microliter valve which is typically used in a chromatograph, not a volumetric primary standard apparatus V as in the present invention. Such microliter valves are currently manufactured by the Arcas Division of Anacon Inc. of Houston, Tex.

The volumetric primary standard apparatus V of the present invention further includes transfer means T for transferring the carrier gas and sample gas therewith from the injection means I to a mixing chamber C. The transfer means T includes conduit 96 mounted in flow communication with the mixture exit port 50d of the valve body 50 and in communication with the chamber C.

The mixing chamber C of the volumetric primary standard apparatus V of the present invention includes a flow-through mixing chamber 98 for receiving carrier gas and sample gas therewith for thorough mixing thereof to form a homogeneous mixture output for continuous flow therefrom for flow to an analyzer A. The mixing chamber 98 includes a first internal chamber 98a, a second internal chamber 98b, a third internal chamber 98c, and a fourth internal chamber 98d. Preferably, the chambers 98a, 98b, 98c, 98d are individually separated by baffle means B for causing effective mixing of the sample gas with the carrier gas when the mixture flows from the first internal chamber 98a into the second, third, and fourth internal chambers 98b, 98c, 98d, respectively. The baffle means B includes a plurality of baffle plates 100, 102, 104, each having openings 100a, 102a, 104a formed therethrough, preferably in an inclined fashion, for causing gas to flow in a non-linear, turbulent flow path as depicted by arrows 106, 108, 110 for enhanced mixing of sample gas and carrier gas therein the mixing chamber 98.

An analyzer A, which may be any suitable type of analyzer, such as a hydrogen sulfide analyzer, is connected to the mixing chamber C by connecting means D. The connecting means D includes conduit 114 which receives the homeogeneous mixture of carrier gas and sample gas flowing in the direction of arrow 116 which is directed into the analyzer A for obtaining a concentration reading of such homogeneous mixture by the analyzer A. The analyzer A may be an analyzer such as disclosed in U.S. Pat. No. 3,756,781 to C. L. Kimball, the inventor of the volumetric primary standard apparatus V of the present invention.

In the use or operation of the volumetric primary standard apparatus V of the present invention, it is of the utmost importance that the carrier gas flow through the flow means F be capable of critical, exacting flow control such that the rate can be very carefully monitored and measured by the flow measuring device 10. On the other hand, flow of the sample gas through flow measuring device 30 need not be of an exacting amount, but rather merely be sufficient to keep the conduits 40, 40a and sample gas inlet port 50a full of sample gas at all times. Similarly, pneumatic air flow, regulated by valve 68, to the timing means M need be only of that flow sufficient to keep the timing means M properly operational, and within those constraints, the amount of flow through the conduits 70, 70a is not critical.

The chambers 60a, 60b, 60c is slider block 60 must be of an identic size for minimum effect on flow pressures. Preferably, each of such chambers 60a, 60b, 60c are of a volume of 0.001 milliliters. Further, injection rates of the injection means I preferably may vary from three to thirty oscillations per minute.

As shown in FIG. 2, chamber 60b receives sample gas flowing in conduit 40a in the direction of arrow 120 and capable of flowing through chamber 60b, sample gas exit port 50b, into conduit 122 affixed in flow communication to sample gas exit port 50b, and outwardly therefrom in the direction of arrow 124. Also as shown in FIG. 2, accurately regulated carrier gas flows in conduit 20a in the direction of arrow 126 into carrier gas inlet port 50c in valve body 50, through chamber 60a in slider block 60, into mixture exit port 50d and outwardly therefrom into transfer means T including conduit 96 in the direction of arrow 128 into mixing chamber C, therefrom the mixing chamber C in the direction of arrow 116 (FIG. 1) into the analyzer A. As such, the chamber 60b of the slider block 60 is filled with sample gas and chamber 60a is filled with carrier gas. As noted hereinabove, with all chambers 60a, 60b, 60c being of the same volume, chamber 60b is filled with a volume of sample gas corresponding to the volume of carrier gas within chamber 60a.

A pneumatic impulse at a selected interval regulated by the timing means M results in pneumatic pressure acting through passageway 64e in the direction of arrow 94, resulting in downward vertical movement of the actuator piston 78, actuator shaft 80, arm 88 and slider block 60. This downward movement results in the FIG. 1 inject position where chamber 60c communicates with the sample gas inlet port 50a and sample gas exit port 50b for flow of sample gas therethrough and outwardly therefrom into conduit 122 in the direction of arrow 124, while chamber 60b now communicates with carrier gas inlet port 50c and mixture exit port 50d. As will be recalled, in the purge position of FIG. 2, chamber 60b was filled with sample gas, but in the inject position of FIG. 1, chamber 60b communicates with the carrier gas such that the sample gas is introduced into the flowing carrier gas stream. Thus, a measured amount for example, 0.001 milliliters corresponding to the volume within chamber 60b, of sample gas within the chamber 60b as shown in FIG. 1 is injected into the carrier gas stream that is accurately regulated by the flow means F. The carrier gas-sample gas mixture flows through the transfer means T into mixing chamber C wherein the non-linear, turbulent flow therein as depicted by arrows 106, 108, 110, 112 enhances the homogeneous mixing of the sample gas and carrier gas. This mixture is thereafter directed into the analyzer A by connecting means D.

Upon appropriate pneumatic impulse of the timing means M, pneumatic pressure through passageway 64d in the direction of arrow 92 results in the upward urging of the actuator piston 78, resulting in movement of the slider block 60 to the purge position of FIG. 2 where again the chamber 60b is again filled with sample gas, with the sample gas within conduit 40a washing any residual carrier gas in chamber 60b therefrom, into conduit 122 and outwardly in the direction of arrow 124 (FIG. 2) to an appropriate discharge or holding tank (not shown). The carrier gas initially trapped within chamber 60a during the inject position of FIG. 1 is thereagain reintroduced into the carrier gas stream to continue the accurate monitoring and flow of the carrier gas stream. As such, chamber 60b oscillates between the sample gas inlet port 50a and carrier gas inlet port 50c resulting in the injection and introducing of the sample gas into the carrier gas stream.

For example, using a 0.001 milliliter chamber, 60a, 60b, 60c and injection rates for the injection means I varying from three to thirty injections per minute, the volumetric primary standard apparatus V may provide anywhere from 0.003 milliliters per minute to 0.030 milliliters per minute of a homogeneous mixture thereof. Further, by way of example, using flow means F to regulate the flow of carrier gas at 3,000 milliliters per minute will correspondingly provide a homogeneous mixture after mixing of one part per million if the injection rate is at three injections per minute. Correspondingly, thirty injections per minute of the injection means I of the sample gas into the carrier gas will result in a homogeneous mixture having a concentration of ten parts per million, if the carrier gas flow is maintained at the 3,000 milliliters per minute rate. As is evident, a plurality of injections can provide multiple parts per million mixtures accurately. Thus, as the sample gas is metered from the chamber 60b whose volume can be accurately maintained into the carrier gas stream, known concentrations of sample gas in a carrier gas stream may be produced wherein troublesome, inaccurate, difficult measurements of varying flow from a permeation tube may be eliminated while further avoiding the need to accurately measure very low flow rates of such mixtures, as taught in the prior art. The volumetric measurement of the sample gas provides ease in maintaining accurate flows, whereas temperature and barometric corrections, necessary in permeation devices, can be eliminated.

The concentration of such a mixture in parts per million may be determined by the simple formulation that:

$$a = [b/(b + c)] \times 10^6$$

where $a$ equals the concentration in parts per million by volume generated, $b$ equals sample gas flow rate and $c$ equals the carrier gas flow rate.

Figure 3:
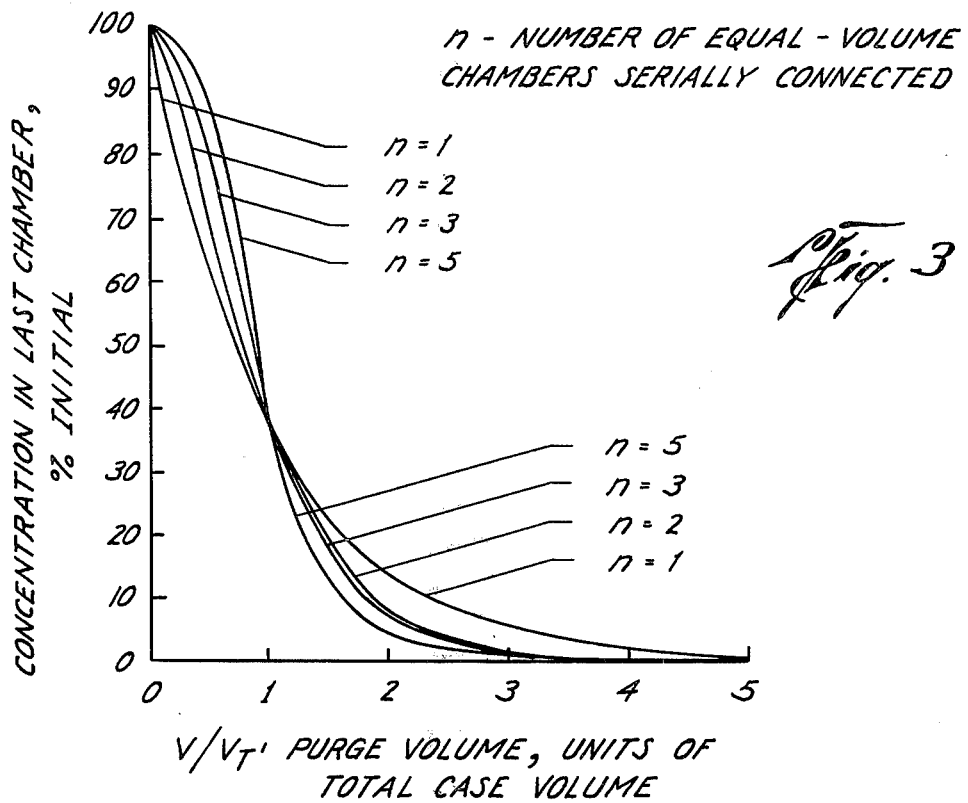
FIG. 3 is a graph detailing the effectiveness of multi-chamber mixing.

As shown in FIG. 3, as the number of equal-volume chambers within the mixing chamber C increase, the more effective mixing occurs therein. In order for effective mixing to occur, it is desirable that the concentration in the last chamber, chamber 98d, in terms of a percentage of the initial concentration of the sample gas, be substantially zero percent. As such, if only one chamber were within the mixing chamber C of the present invention, the ratio of purge volume to total volume must reach almost five in order to reach the zero percent concentration level as shown on the graph of FIG. 3. However, in contradistinction, if, for example five chambers were serially connected in the mixing chamber C, the concentration in the last chamber would approach the zero percent initial concentration between the three-four purge volume to total volume indices and also would be below the 10% initial concentration at a ratio less than 2. As is evident, dramatic increases are manifest as far as mixing, by merely increasing the number of internal chambers within the mixing chamber C, with less significant mixing results being evident as the number of chambers increase thereafter. However, suffice to say that multiple chambers such as the four depicted in the mixing chamber C of FIG. 1 will help to insure that the output thereof directed in the direction of arrow 116 from the mixing chamber C into the analyzer A will be homogeneous, having no isolated concentration levels of sample gas within the carrier gas streams.

Figure 4:
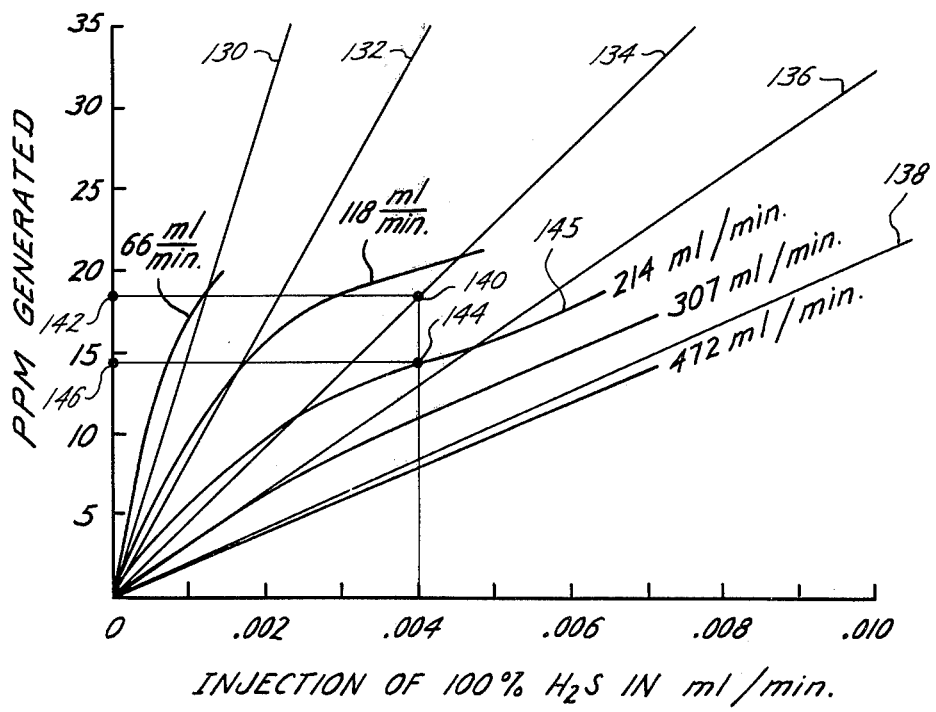
FIG. 4 is a graph representative of those to be used in conjunction with the volumetric primary standard apparatus and method of the present invention for determining the accuracy of analyzer readings.

In practicing the method of the present invention, it is necessary that one understand the graph as set forth in FIG. 4. As noted hereinabove, concentration may be mathematically calculated in accordance with:

$$a = [b/(b + c)] \times 10^6$$

At specified flow rates of carrier gas with specific injection rates of sample gas, lines indicating the computed concentrations may be graphically represented. For example, line 130 relates to a carrier gas flow of 66 milliliters per minute, while line 132 relates to a carrier flow of 118 milliliters per minute, line 134 relates to a carrier flow of 214 milliliters per minute, line 136 relates to a carrier flow of 307 milliliters per minute, while line 138 relates to a carrier flow of 472 milliliters per minute. For example, using a carrier gas flow rate of 214 milliliters per minute and an injection rate of sample gas of 0.004 milliliters per minute at point 140 on line 134, using the above-identified formulation, the concentration would equal:

$$a = [0.004/(214 + 0.004)] \times 10^6 = 18.6 \text{ PPM}$$

which may be read directly at point 142 on the graph of FIG. 4.

Reference concentrations may be established by use of static procedures wherein fixed volumes of carrier gas have known quantities of sample gas injected therein to provide known parts per million concentration sample gas in such mixtures. Such known concentration samples of mixtures may in turn be compared with dynamic results in order to determine the accuracy of such results. In using the dynamic system of the volumetric primary standard apparatus V of the present invention, it has been experimentally determined that the mathematical concentrations are not exactly reproducible by using such apparatus V. However, by using known concentration references, graphs indicating actual performance at a given carrier flow rate and a given injection of sample gas, result in identification of specific concentrations of parts per million mixtures. For example, using the 214 milliliter per minute flow rate used above and an injection rate of sample gas at 0.004 milliliters per minute, rather than resulting in the 18.6 PPM concentration at point 142 from referencing at point 140, actual testing with a flow of 214 milliliters of carrier gas, using a plurality of injection rates of sample gas has resulted in actual performance indicated by graph line 145. Using graph line 145 and an injection rate of 0.004 milliliters per minute results in arriving at point 144 on line 145, providing the true concentration indicator, which when translated in terms of parts per million generated, results in one being able to read point 146 on the graph of FIG. 4, approximating a concentration representation of 14 parts per million rather than the expected, theoretical 18.6 results indicated by point 142. As is evident, the graph of FIG. 4 has been reduced in size and in scale to effectively represent the procedures utilized in the apparatus V of the present invention, however, by expanding the scales on both the X and Y axis thereof, accurate concentrations in parts per million may be represented and interpreted directly from readings of such a graph as in FIG. 4. It is anticipated that the diversity between the mathematical, theoretical concentration and the actual concentration is due to a number of factors, the most significant being that within the chamber such as chamber 60b of the slider block 60, there is wetting of the interior surface thereof by the sample gas due to the molecular differences between the material of the slider block and that of the sample gas. For example, should the sample gas be hydrogen sulfide, which is typically a polar material, such has a tendency to "stick" or adhere to the surface of the chamber and/or resulting in adsorption of the gas on the surface of the chamber 60b. As might be expected, as the flow rates of the carrier gas increase, the closer the actual readings track the mathematical calculations. For example, at a flow rate of carrier gas of 118 milliliters per minute, the actual readings in concentrations fall off dramatically from the theoretical at approximately the 0.002 injection rate of sample gas. However, comparison of the 472 milliliter per minute flow rate of carrier gas most nearly tracks the theoretical, calculated line 138 at all injection rates. This occurs because as the flow rate of the carrier gas increases, there is greater opportunity for the chamber such as chamber 60b, having all of the sample gas entrapped therein, to be "washed" from that chamber by the high rate flowing carrier gas, thus more fully injecting the sample gas into the flowing carrier gas stream. Therefore, the actual test readings tend to more nearly parallel the theoretical results at high flow rates of carrier gas.

In performing the method of testing an analyzer A to determine the accuracy thereof of the present invention, it is first necessary to flow the carrier gas stream at a known flow rate, with such being monitored accurately by flow means F. Thereafter, it is necessary to periodically inject a measured quantity of the sample gas at a selected interval into the carrier gas stream. The periodic injection is accomplished by the injection means I as regulated by the timing means M. Thereafter the carrier gas and sample gas are homogeneously mixed in the mixing chamber C for providing a homogeneous mixture of sample gas and carrier gas, with the homogeneous mixture being thereafter flowed into the analyzer A whose accuracy is to be tested. The homogeneous mixture flowing into the analyzer results in obtaining a concentration reading of the homogeneous mixture with the analyzer A. This concentration reading of the analyzer A may be compared with the chart of FIG. 4 to determine whether or not the analyzer A is initially properly working. Therefore, if by way of example, the carrier stream flow rate were at 214 milliliters per minute and the injection rate of sample gas was 0.004 milliliters per minute, it would be expected that the analyzer would be reading concentration readings of approximately 14 parts per million as indicated by point 146.

Thereafter, the analyzer may be used for testing a gas having an unknown concentration of sample gas by removing flow from the volumetric primary standard apparatus V of the present invention and introducing such unknown concentration gas into the analyzer A. One may obtain a concentration reading of the unknown concentration of sample gas by the analyzer A. At this point, the analyzer may be used for a selected period of time for obtaining numerous concentration readings of unknown samples of carrier gas and sample gas for determining concentrations of such sample gas in the carrier gas stream. During the determination of concentrations of unknown mixtures of carrier gas and sample gas, the volumetric primary standard apparatus V of the present invention is not in use, with such unknown flows being fed directly into the analyzer A.

When it is desirous to verify the authenticity and reliability of the results as provided by the analyzer A, the carrier gas-sample gas stream of unknown concentration is merely switched off and flow is directed to the analyzer A using the volumetric primary standard apparatus V of the present invention as described hereinabove, by using the known flow rate of carrier gas, a known rate of injecting of sample gas into the carrier stream, the homogeneous mixing of the carrier gas and sample gas, and flowing the homogeneous mixture into the analyzer A to be tested. With this mixture flowing through the analyzer A, the analyzer A will result in providing a concentration reading which is to be compared with the previously determined concentrations of sample gas in the carrier gas at the known flow rates of carrier gas and at the selected rate of injection of the sample gas into the carrier gas to rapidly determine whether the readings of the analyzer A are accurate. Thus, for example, by setting the injection of sample gas at 0.004 milliliters per minute and having a carrier gas flow of 214 milliliters per minute, the analyzer concentration reading should track 14 parts per million as determined by use of the FIG. 4 graph at point 146. If the concentration reading of the analyzer A does in fact so track the concentration reading provided by using the known flow rate of carrier gas and known inject rate of sample gas then, the veracity of the readings of the analyzer A is established. However, should a diversity of concentration readings from that as actually produced by the analyzer A and that that should be produced in accordance with the parameters set forth in the chart of FIG. 4, then it is known that there is error in the analyzer A and that the readings thereof are not accurate, nor providing good information.

If the analyzer is not reading properly, then such may be recalibrated by using known techniques such as a static technique wherein a known volume of carrier gas has a known volume of sample gas mixed therein, providing a known concentration mixture for appropriately recalibrating the analyzer A. On the other hand, if the analyzer A is reading correctly, then the volumetric primary standard apparatus V of the present invention is merely deactivated, and the analyzer A thereagain used for determining concentration levels in carrier gas streams having unknown quantities of sample gas therein.

It will be appreciated that use of the volumetric primary standard apparatus V and method of the present invention provides an apparatus and method that may be easily and rapidly used for providing periodic checks of the analyzer A. For example, the analyzer A may be used for an hour and then the procedures outlined hereinabove be utilized to rapidly determine whether the readings of the analyzer A are accurate. If so, then the analyzer A may be thereagain utilized in determining such unknown concentrations. Thus, the analyzer may be easily and quickly tested, even multiple times within short time periods, for determining the accuracy and reliability of its readings. Furthermore, the volumetric primary standard apparatus V and method of this invention do not suffer from the infirmities of the prior art in that barometric pressure and temperature are not significant in the overall testing procedure as is the case in the permeation devices of the prior art.

In order for the volumetric primary standard apparatus V to operate properly, it is preferred that the flow rate of carrier gas be at least 25% greater than the flow rate of the sample gas to be directed through the analyzer A. Thus, simply stated, the volumetric primary standard apparatus V and method of the present invention eliminates all variables except for one, namely, the reliability of the readings of the analyzer A, such that the analyzer A may be quickly, effectively and reliably tested for accuracy.

The foregoing disclosure and description of the invention are illustrative and explanatory thereof, and various changes in the size, shape and materials as well as in the details of the illustrated construction may be made without departing from the spirit of the invention.

I claim:

1. A volumetric primary standard apparatus for providing a standard for rapidly and frequently determining whether the readings of an analyzer are accurate, comprising:
   flow means for flowing a carrier gas at a known rate;
   injection means connected to said flow means for injecting periodic measured amounts of sample gas at selected intervals into said carrier gas as it is flowing through said injection means;
   transfer means for transferring the carrier gas and said sample gas therewith from said injection means to a mixing chamber; and,
   a flow-through mixing chamber for receiving said carrier gas and said sample gas therewith for thorough mixing thereof to form a homogeneous flowing mixture and for continuous flow therethrough for flow to an analyzer at a substantially constant concentration.

2. The volumetric primary standard apparatus of claim 1, wherein said injection means includes:
   a valve body having a sample gas inlet port, a sample gas exit port, a carrier gas inlet port, and a mixture exit port; and,
   regulating means for regulating the communication of said sample gas within said sample gas inlet port with said carrier gas in said carrier gas inlet port to be discharged from said valve body through said mixture exit port into said mixing chamber.

3. The volumetric primary standard apparatus of claim 2, wherein:
   said regulating means includes a slider block movable from a purge position to a inject position;
   said slider block having a first chamber, a second chamber, and a third chamber;
   said slider block having said first chamber communicating with said carrier gas inlet port and said mixture exit port and said second chamber communicating with said sample gas inlet port and said sample gas exit port when in said purge position; and,
   said slider block having said second chamber communicating with said carrier gas inlet port and said mixture exit port and said third chamber communicating with said sample gas inlet port and said sample gas exit port when in said inject position.

4. The volumetric primary standard apparatus of claim 1, including:
   timing means mounted with said injection means for regulating the rate of injection of said sample gas into said carrier gas at said selected intervals.

5. The volumetric primary standard apparatus of claim 1, wherein:
   said mixing chamber includes at least a first internal chamber and a second internal chamber separated by baffle means for causing effective mixing of said sample gas with said carrier gas when said mixture flows from said first internal chamber into said second internal chamber.

6. The volumetric primary standard apparatus of claim 5, wherein:
   said baffle means includes a plurality of baffle plates each having openings formed therethrough for causing the gas to flow in a non-linear, turbulent flow path.

7. The volumetric primary standard apparatus of claim 1, further including:
   an analyzer; and,
   connecting means for connecting said mixing chamber with said analyzer for receiving said gas for testing and accurately calibrating the analyzer.

8. A method of testing an analyzer to determine the accuracy thereof, comprising the steps of:
   flowing a carrier gas stream at a known flow rate;
   periodically injecting a measured quantity of sample gas at selected intervals into the carrier gas stream as the carrier gas is flowing;
   homogeneously mixing the carrier gas and the sample gas therewith in a mixing chamber for providing a homogeneous mixture of the sample gas and carrier gas at a substantially constant concentration, and,
   flowing the homogeneous mixture into an analyzer whose accuracy is to be tested.

9. The method of claim 8, further including the step of:
   obtaining a concentration reading of the homogeneous mixture with the analyzer.

10. The method of claim 9, further including the step of:
    introducing a gas having an unknown concentration of sample gas into the analyzer; and
    obtaining a concentration reading of the unknown concentration of sample gas by the analyzer.

11. The method of claim 10, further including the step of:
    comparing the concentration reading of the analyzer with a previously determined concentration of the sample gas in the carrier gas at the known flow rate of the carrier gas and at the selected rate of injection of the sample gas into the carrier gas to rapidly determine whether the readings of the analyzer are accurate.

12. The method of claim 11, wherein the previously determined concentrations for comparison with readings obtained with the flowing carrier gas and injected sample gas are utilized by:

making a record of the previously determined concentration readings of the analyzer for comparing the accuracy thereof with a plurality of different fixed volume, known concentration homogeneous mixtures.

13. The method of claim 8, wherein said periodically injecting is accomplished by a volumetric primary standard apparatus including a valve body having a movable slider block therein, the slider block having plural chambers formed therein to receive sample gas and carrier gas for mixing, further including the step of:

adjusting the volume of the plural chambers to compensate for the adherence of the sample gas to the walls of the chambers for generating an accurate homogeneous mixture.

14. The method of claim 13, further including the step of:

preparing graphs by referencing the homogeneous mixture output of the volumetric primary standard apparatus to a mixture obtained by static mixing of volumes of carrier gas and sample gas to provide a measure for correcting the volume of the chambers in the slider block to provide a selected concentration of homogeneous mixture.

* * * * *